(12) United States Patent
Zardini (10) Patent No.: US 10,722,321 B2
(45) Date of Patent: Jul. 28, 2020

(54) WASHING DEVICE FOR MEDICAL INSTRUMENTS

(71) Applicant: STEELCO SPA, Riese Pio X (IT)

(72) Inventor: Fabio Zardini, Castelfranco Veneto (IT)

(73) Assignee: STEELCO SPA, Riese Pio X (IT)

( * ) Notice: Subject to any disclaimer, the term of this patent is extended or adjusted under 35 U.S.C. 154(b) by 0 days.

(21) Appl. No.: 15/034,816

(22) PCT Filed: Nov. 7, 2014

(86) PCT No.: PCT/IB2014/065872
§ 371 (c)(1),
(2) Date: May 5, 2016

(87) PCT Pub. No.: WO2015/068131
PCT Pub. Date: May 14, 2015

(65) Prior Publication Data
US 2016/0287350 A1    Oct. 6, 2016

(30) Foreign Application Priority Data
Nov. 7, 2013   (IT) .............................. UD2013A0146

(51) Int. Cl.
*A61B 90/70* (2016.01)
*A61B 1/12* (2006.01)
(Continued)

(52) U.S. Cl.
CPC .............. *A61B 90/70* (2016.02); *A61B 1/123* (2013.01); *A61B 1/125* (2013.01); *A61M 39/105* (2013.01);
(Continued)

(58) Field of Classification Search
CPC ......... B08B 3/08; B08B 9/0323; B08B 9/023; A61B 90/70; A61L 2/00; A61L 2/04;
(Continued)

(56) References Cited

U.S. PATENT DOCUMENTS 2,509,444 A * 5/1950 Mitchell ............... F16L 37/252
137/614.04
4,247,135 A * 1/1981 Weirich .................. E21D 23/26
285/124.4
(Continued)

FOREIGN PATENT DOCUMENTS

DE   3819257 C1   7/1989
EP   1 728 465 A1   12/2006
(Continued)

OTHER PUBLICATIONS

Search Report and Written Opinion for PCT/IB2014/065872, dated Feb. 5, 2015.

*Primary Examiner* — Joseph L. Perrin
*Assistant Examiner* — Kevin G Lee
(74) *Attorney, Agent, or Firm* — Marshall, Gerstein & Borun LLP (57) ABSTRACT

A washer machine for medical instruments comprises a washing chamber, at least a sliding loader trolley at least to load the medical instruments into the washing chamber and a washing device to wash the medical instruments, comprising a multiple connection unit and a plurality of flexible washing pipes connectable to the aperture of the medical instrument to be washed. The multiple connection unit comprises a free multiple connector, autonomous and unconstrained from the sliding loader trolley and connectable to said flexible washing pipes, and a static and fixed multiple counter-connector disposed in the washing chamber. A releasable manual mechanical clamping device is (Continued)

provided for the selective connection of the free multiple connector to the static and fixed multiple counter-connector.

9 Claims, 3 Drawing Sheets (51) Int. Cl.
    *A61M 39/10*     (2006.01)
    *F16L 37/56*     (2006.01)
    *F16L 39/02*     (2006.01)
    *B08B 3/08*     (2006.01)
    *B08B 9/023*     (2006.01)
    *B08B 9/032*     (2006.01)

(52) U.S. Cl.
    CPC .............. *B08B 3/08* (2013.01); *B08B 9/023* (2013.01); *F16L 37/56* (2013.01); *F16L 39/02* (2013.01); *B08B 9/0323* (2013.01)

(58) Field of Classification Search
    CPC ... A61L 2/07; F16L 39/00; F16L 39/02; F16L 11/22; F16L 37/56; F16L 37/14; F16L 37/60; A61M 39/105
    USPC .......................................................... 600/132
    See application file for complete search history.

(56) References Cited

U.S. PATENT DOCUMENTS

| | | | | |
|---|---|---|---|---|
| 4,630,847 A | * | 12/1986 | Blenkush | F16L 37/56 |
| | | | | 285/242 |
| 6,558,620 B1 | * | 5/2003 | Sanford | A61B 1/123 |
| | | | | 134/102.2 |
| 7,651,672 B2 | * | 1/2010 | Lin | A61L 2/186 |
| | | | | 134/22.11 |
| 2004/0091389 A1 | | 5/2004 | Malkin et al. | |
| 2007/0100206 A1 | * | 5/2007 | Lin | A61B 1/123 |
| | | | | 600/156 |
| 2013/0147185 A1 | * | 6/2013 | Tsao | A61M 39/1011 |
| | | | | 285/120.1 |

FOREIGN PATENT DOCUMENTS

| | | |
|---|---|---|
| EP | 1 815 782 A2 | 8/2007 |
| EP | 1 949 868 B1 | 12/2010 |
| EP | 2 445 438 A1 | 5/2012 |

* cited by examiner fig. 1 fig. 2 fig. 3 fig. 4

WASHING DEVICE FOR MEDICAL INSTRUMENTS

FIELD OF THE INVENTION

The present invention concerns a washer machine for medical instruments of the tubular type made of various materials, in particular metal, plastic and/or rubber, used in medicine to explore and examine using optical equipment, or to empty natural cavities of the body, and introduced by natural or artificial paths. In particular, the washer machine can be used for washing, chemical disinfecting, drying and cleaning of one or more instruments of the endoscopic type such as colonoscopes, broncoscopes and gastroscopes.

BACKGROUND OF THE INVENTION

Washer machines are known, for washing medical instruments of the endoscopic type, used during clinical practice. Known machines of the type in question are described for example in the European patent EP-B-1.949.868 (EP'868) and in the European patent application EP-A-2.445.438 (EP'438).

Endoscopic instruments typically include an operative flexible pipe, also called insertion pipe, suitable to be inserted into the patient's body, with a length and diameter which vary according to applications. Inside the operative flexible pipe channels of various sizes and for various uses can be disposed or made, for example for a biopsy, inspection using a video camera, for lighting, to spray air and/or water.

Washer machines typically include a washing chamber, in which the complete washing treatment is carried out both on the external surfaces and on the internal surfaces and channels of the endoscopic instrument, using washing liquids, such as water and detergents or chemical disinfectants, for example with a glutaraldehyde or peracetic acid base.

The external surface of the endoscopic instrument is treated, typically by immersion in a container, for example an auxiliary tube, positioned in the washing chamber and connected to the washing circuit by means of a sleeve. Alternatively, this treatment can be done using a washing device as described for example in EP'868 or EP'438.

The internal surfaces are treated by connecting flexible pipes to the internal channels of the endoscopic instrument.

In particular, the flexible pipes include at one end the attachment connectors to the internal channels of the endoscopic instrument, and at the other end coupling connectors to a suitable hermetically sealed multiple connector.

The hermetically sealed multiple connector is configured to connect the endoscope to devices that deliver the washing liquid.

At least one sliding trolley is provided, which functions as a loading container inside the washing chamber, on which the endoscopic instrument is laid. The sliding trolley, or loading container, includes in its structure the hermetically sealed connector, which is thus on board the sliding trolley.

An example of a loading container is described in EP'868 or EP'438.

The sliding trolley or loading container is selectively mobile from the inside to the outside of the washing chamber and vice versa.

Typically, the closing door is opened, to allow access inside the washing chamber and the sliding trolley is removed from the washing chamber, but remains connected to the washer machine, resting on a support plane or suspended cantilevered, to allow the staff responsible to position the endoscopic instrument, while the closing door remains always open and the machine, in fact, is not operative, in order to give the operator time to perform the required positioning and connections.

The endoscopic instrument is not only connected by its internal channels to each of the washing pipes and tubes, in their turn to be connected to the corresponding connectors of the hermetically sealed multiple connector provided on board and integrated with the sliding trolley, but is also placed in a suitable position for washing, that is, where there is no narrowing of the internal channels, usually rolled in a circular way or in a spiral.

When the sliding trolley is made to re-enter the washing chamber, after the positioning of the endoscopic instrument, the multiple connector is connected, with a pneumatically actuated connection head, to a multiple counter-connector in turn communicating with the washing circuit.

One disadvantage of known washer machines is that the operations for positioning the endoscopic instrument and connecting it to the flexible pipes carried out directly on the sliding, extractable trolley cause downtimes in the washing process, since they are essentially carried out on the machine, with the machine stopped, which translates into low productivity of the washer machine.

Another disadvantage of such washer machines is that the automatic pneumatic connection between the multiple connector on board the trolley and washing circuit represents a mechanical encumbrance and a considerable complication in terms of components and circuit, and can represent one of the causes of malfunction of the machine and therefore the stoppage of the machine.

Document DE-C-3819257 describes a washing and disinfecting device for medical instruments of the known type.

Document US-A-2004/0091389 describes an apparatus to re-process flexible endoscopes with steam.

There is therefore the need to perfect a washer machine that can overcome at least one of the disadvantages of the state of the art.

In particular, one purpose of the present invention is to produce a washer machine that allows to increase productivity, thanks to a reduction in downtimes and that simplifies and facilitates the operations to position and/or connect the endoscopic instrument to the washer machine.

Another purpose of the present invention is to produce a more reliable washer machine in which the probability of breakdowns and therefore stoppages of the machine for repairs, maintenance and replacements are reduced.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purposes, forms of embodiment described here concern a washer machine for medical instruments, including a washing chamber, at least a sliding trolley for loading the medical instruments into the washing chamber and a washing device for washing the medical instruments, including a multiple connection unit and a plurality of flexible washing pipes which can be connected to apertures of the medical instrument to be washed. According to the present description, the multiple connection unit includes a free multiple connector, autonomous and unconstrained from the sliding loader trolley and connectable to the flexible washing pipes, and a static and fixed multiple counter-connector disposed in the washing chamber, a releasable manual mechanical clamping device being provided for the selective connection of the free multiple connector to the static and fixed multiple counter-connector.

According to possible forms of embodiment, the free multiple connector can include a plurality of individual connectors, each connectable on one side to the flexible washing pipes and on the other side connectable to mating individual counter-connectors provided in the static and fixed multiple counter-connector.

According to possible forms of embodiment, the free multiple connector can include a connector support body, configured to support the individual connectors, and a flexible pipe collector body.

According to possible forms of embodiment, the static and fixed multiple counter-connector can include a counter-connector support body, configured to support the individual counter-connectors.

According to possible forms of embodiment described here, the releasable manual mechanical clamping device can be the rotary type, in particular with rotating attachment, that is, it can be activated by means of rotation, for example by the user or operator.

These and other aspects, characteristics and advantages of the present disclosure will be better understood with reference to the following description, drawings and attached claims. The drawings, which are integrated and form part of the present description, show some forms of embodiment of the present invention, and together with the description, are intended to describe the principles of the disclosure.

The various aspects and characteristics described in the present description can be applied individually where possible. These individual aspects, for example aspects and characteristics described in the attached dependent claims, can be the object of divisional applications.

It is understood that any aspect or characteristic that is discovered, during the patenting process, to be already known, shall not be claimed and shall be the object of a disclaimer.

BRIEF DESCRIPTION OF THE DRAWINGS

These and other characteristics of the present invention will become apparent from the following description of some forms of embodiment, given as a non-restrictive example with reference to the attached drawings wherein.

To facilitate comprehension, the same reference numbers have been used, where possible, to identify identical common elements in the drawings. It is understood that elements and characteristics of one form of embodiment can conveniently be incorporated into other forms of embodiment without further clarifications.

DETAILED DESCRIPTION OF A FORM OF EMBODIMENT

We shall now refer in detail to the various forms of embodiment of the present invention, of which one or more examples are shown in the attached drawing. Each example is supplied by way of illustration of the invention and shall not be understood as a limitation thereof. For example, the characteristics shown or described insomuch as they are part of one form of embodiment can be adopted on, or in association with, other forms of embodiment to produce another form of embodiment. It is understood that the present invention shall include all such modifications and variants.

Figure 1:
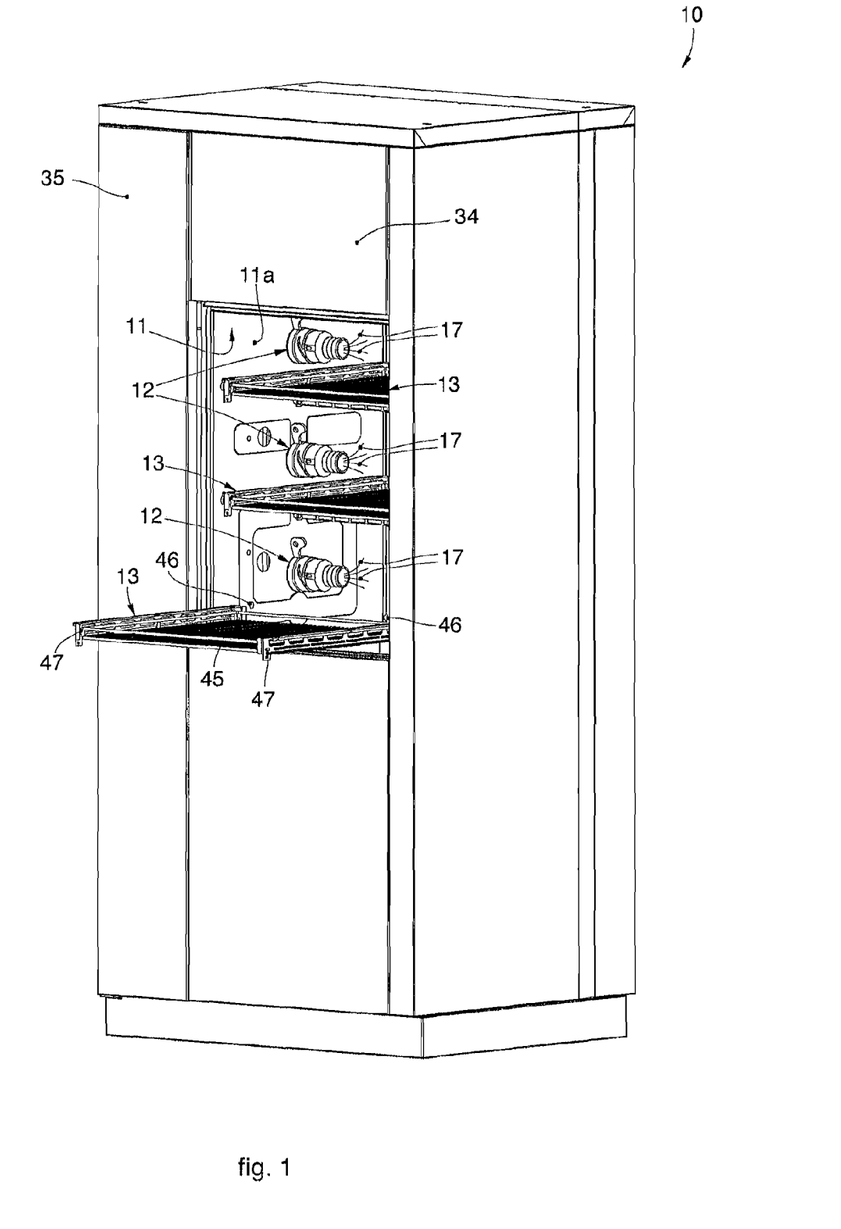
FIG. 1 is a perspective view of forms of embodiment of a washer machine for endoscopic instruments according to the present invention.

FIG. 1 is used to describe forms of embodiment of a washer machine 10 for medical instruments, such as for example endoscopic instruments, according to the present description.

In some forms of embodiment, the washer machine 10 can be configured to wash the external surfaces and/or the internal surfaces of the endoscopic instruments in question.

The washer machine 10 includes a washing chamber 11 and at least one sliding loader trolley 13, for example for loading the endoscopic instruments into the washing chamber 11, and also for removing them.

According to the present description, the washer machine 10 includes a washing device 12 for the endoscopic instruments. The washing device 12 can be used to treat the internal surfaces and possibly also the external surfaces of the endoscopic instruments.

According to possible implementations, the washing device 12 can be configured to connect the endoscopic instrument to an internal washing circuit (not shown) of the washer machine 10.

For example, the internal washing circuit of the washer machine 10 can be configured to convey pre-washing or washing liquids, such as water and detergents or chemical disinfectants, for example with a glutaraldehyde or peracetic acid base, or drying air or other.

According to the present description, the washing device 12 can include a multiple connection unit 12a and a plurality of flexible washing pipes 17, each connected, typically hermetically sealed, at one of their ends to the multiple connection unit 12a. Typically, the flexible washing pipes 17 can each be connected at another end, for example provided with suitable connectors 17a (see FIG. 2 for example), to entrances or apertures of the endoscopic instrument in question, in turn communicating with internal channels of the endoscopic instrument.

According to some forms of embodiment, which can be combined with all the forms of embodiment described here, the multiple connection unit 12a can include a free multiple connector 14 and a static and fixed multiple counter-connector 15, selectively connectable to each other, advantageously hermetically sealed, by means of a releasable manual mechanical clamping device 16.

In possible implementations, the releasable manual mechanical clamping device 16 can be for example the rotary type, in particular with rotating attachment, that is, it can achieve the selective clamping following activation by rotation.

Figure 2:
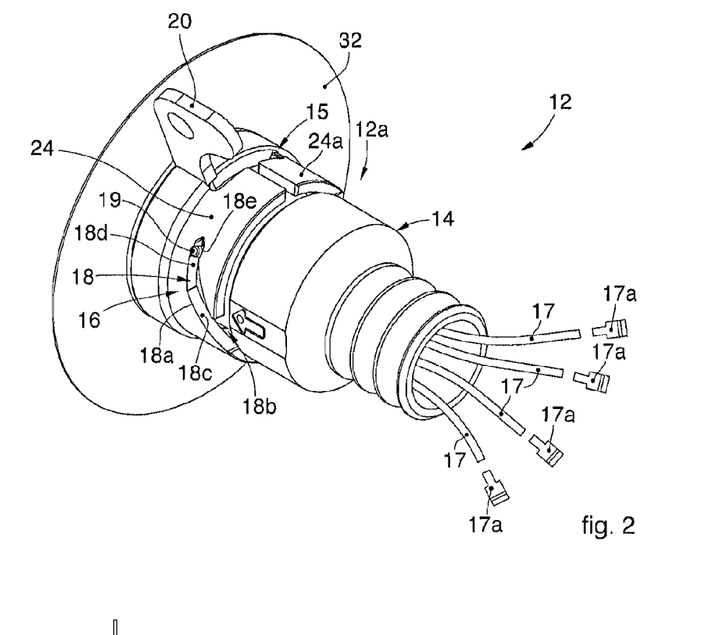
FIG. 2 is a perspective view of forms of embodiment of a washing device comprised in a washer machine according to the present invention.
Figure 3:
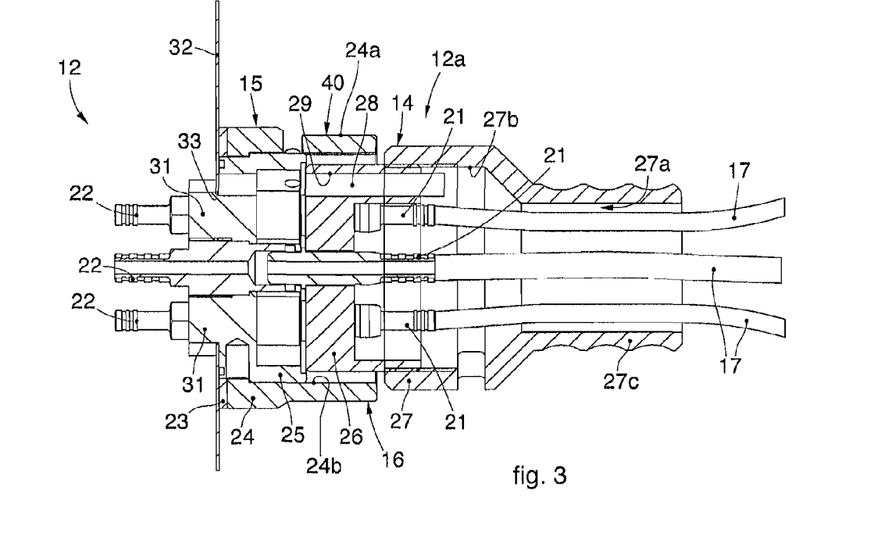
FIG. 3 is a section view of forms of embodiment of a washing device in a washer machine according to the present invention.
Figure 4:
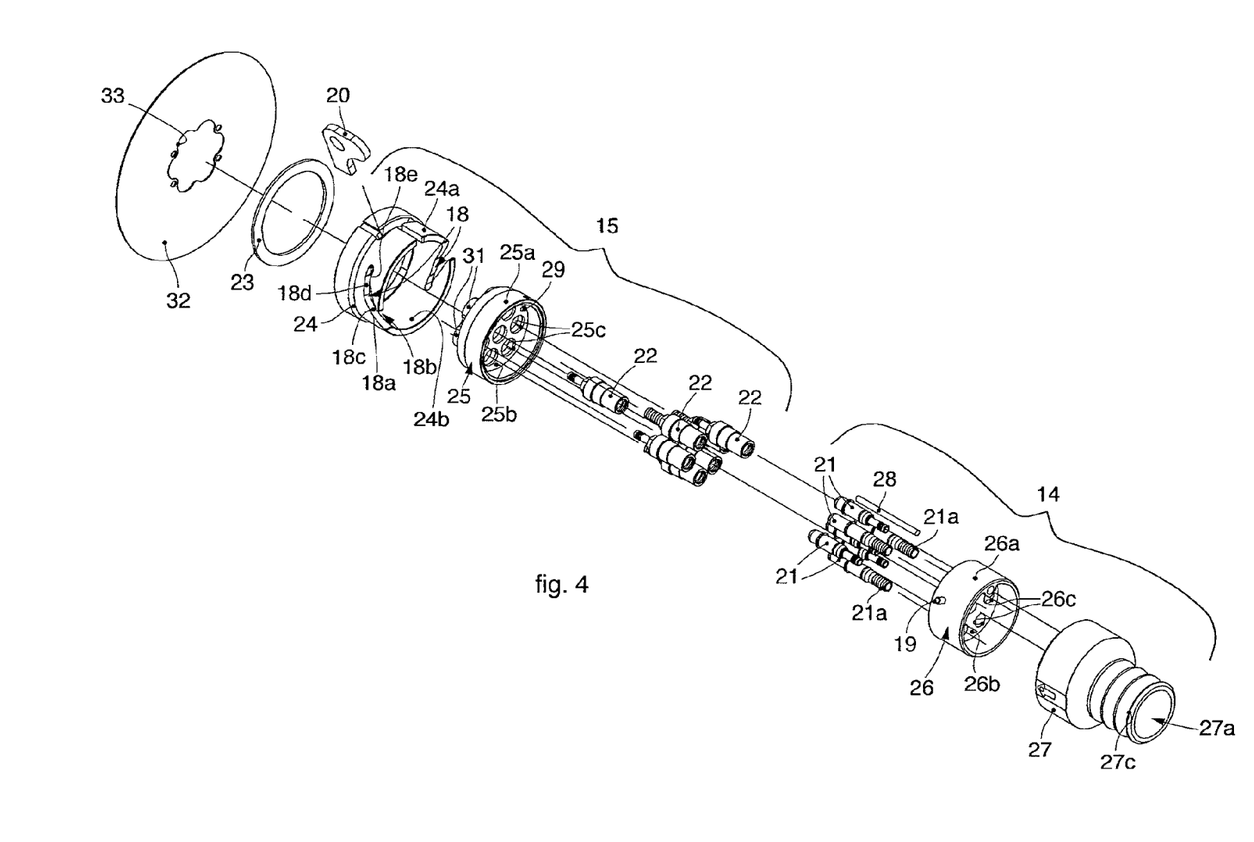
FIG. 4 is a perspective view in separate parts of forms of embodiment of a washing device comprised in a washer machine according to the present invention.

According to some forms of embodiment, which can be combined with all the forms of embodiment described here, the static and fixed multiple counter-connector 15 can be mounted fixed in the washing chamber 11 of the washer machine 10 described here, for example using an assembly plate 32 (see FIGS. 2, 3 and 4 for example). For example, the static and fixed multiple counter-connector 15 can be disposed laterally, on a lateral wall 11a of the washing chamber 11. The static and fixed multiple counter-connector 15 can be made suitably protruding toward the inside of the washing chamber 11 to facilitate the connection with the free multiple connector 14.

According to some forms of embodiment, which can be combined with all the forms of embodiment described here, the free multiple connector 14 is instead autonomous and free from the sliding loader trolley 13, as well as able to be separated on each occasion from the static and fixed multiple counter-connector 15, and can therefore be freely taken, moved and distanced with respect to the washer machine 10 by an operator.

Advantageously, therefore, the operator can easily take the free multiple connector 14, transport it and go to a suitable work bench or surface, which will be for example more comfortable, stable, safe and practical, where he can easily attach to it the flexible washing pipes 17, which in turn have already been connected, for example, to the apertures in the endoscopic instrument to be treated.

In this way, meanwhile, the washer machine 10 can continue to operate or start a treatment cycle on an endoscopic instrument already connected and loaded in the washing chamber 11, since the operation to connect the flexible washing pipes 17 to a specific washing device 12 can even take place separately from the washer machine 10 itself.

It is therefore possible to prepare an array of endoscopic instruments already connected to the flexible washing pipes 17, in turn already connected to the free multiple connector 14, and to load them in series, one after the other at the end of each treatment cycle, without downtimes or stoppages of the machine, and hence with high productivity.

At the start of each new treatment cycle, it is sufficient for the operator to disconnect the free multiple connector 14 from the static and fixed multiple counter-connector 15, acting on the releasable manual mechanical clamping device 16 from inside the washing chamber 11, advantageously by means of an easy and intuitive rotation operation, for example clock-wise, and remove the endoscopic instrument treated and connected to the free multiple connector 14, and to connect another free multiple connector 14 already prepared and in turn connected to other flexible washing pipes 17 and to another endoscopic instrument to be treated, always by means of a simple rotation, for example clock-wise. The operator can transport the combination consisting of the multiple connector 14 already connected to the flexible washing pipes 17 in turn connected to the endoscopic instrument to be treated for example using a transport and containing tray, which can be more manageable and which can subsequently be easily positioned on the sliding loader trolley 13 and inserted into the washing chamber 11.

In this way, by reducing or essentially zeroing the connection downtimes in which the washer machine 10 would be stopped because of the connection times known in the state of the art, and while waiting for loading, productivity is instead considerably increased.

According to some forms of embodiment, described for example using FIGS. 2, 3 and 4, and which can be combined with all the forms of embodiment described here, the free multiple connector 14 can include a plurality of individual connectors 21, each connectable on one side to the flexible washing pipes 17.

In possible implementations, for example the individual connectors 21 can in particular have respective pipe connection ends 21a, for example knurled, toothed or threaded, for stable connection to the flexible washing pipes 17.

Furthermore, the individual connectors 21 can be connected for example on the other side to the static and fixed multiple counter-connector 15, in particular to mating individual counter-connectors 22 provided in the static and fixed multiple counter-connector 15.

For example, to this purpose, in a coordinated manner, the static and fixed multiple counter-connector 15 can be provided with a plurality of said individual counter-connectors 22, equal in number to the individual connectors 21 and configured to receive and couple with the individual connectors 21, advantageously hermetically, for example by same shape or geometric coupling.

In possible implementations, the individual connectors 21 can be the male type and the individual counter-connectors 22 can be the female type (as described for example with reference to FIGS. 3 and 4), or vice versa.

According to some forms of embodiment, described for example using FIGS. 2, 3 and 4, and which can be combined with all the forms of embodiment described here, the free multiple connector 14 can include a connector support body 26, configured to support the plurality of individual connectors 21. For example, the connector support body 26 can include a support bushing 26a which has inside it a transverse wall 26b provided with connector holes 26c for the passage of said individual connectors 21.

According to some forms of embodiment, described for example using FIGS. 2, 3 and 4, and which can be combined with all the forms of embodiment described here, the free multiple connector 14 can include a flexible pipe collector body 27, inside which the flexible washing pipes 17 can be inserted, for example grouped together in a bundle, once connected to the individual connectors 21 (see FIG. 3 for example). The flexible pipe collector body 27 can have, for example, a configuration with a through central cavity 27a, for the passage of the flexible washing pipes 17, with a housing seating 27a to at least partly receive and contain the connector support body 26 on the one side and, on the other side, a connection element 27b, such as a protruding tang or similar element, for example defined by a protrusion with a narrowed section (see FIGS. 3 and 4 for example), for connection to the endoscopic instrument to be treated.

According to some forms of embodiment, described for example using FIGS. 2, 3 and 4, and which can be combined with all the forms of embodiment described here, the static and fixed multiple counter-connector 15 can include a counter-connector support body 25, configured to support said plurality of individual counter-connectors 22. The counter-connector support body 25 can abut frontally against the connector support body 26, so that the individual connectors 21 can couple and connect fluidically with the respective individual counter-connectors 22.

For example, the counter-connector support body 25 can include a support bushing 25a that has inside it a transverse wall 25b provided with counter-connector holes 25c for the insertion of the individual counter-connectors 22.

The counter-connector support body 25 can have, for example, on the side opposite that where the individual counter-connectors 21 are inserted into the individual counter-connectors 22, a mating plurality of connection sockets 31, aligned and communicating with the individual counter-connectors 22, provided for connection to the washing circuit of the washer machine 10, advantageously each, or individually or in groups, dedicated to a specific delivery of washing and/or drying fluid, gas, steam or liquid.

According to some forms of embodiment, described for example using FIGS. 2, 3 and 4, and which can be combined with all the forms of embodiment described here, the releasable manual mechanical clamping device 16 can be the rotating attachment type, and to this purpose can include a clamping bushing 24, attachable for example to the connector support body 26, by rotating the latter. In particular, the clamping bushing 24 can for example be configured to cooperate in rotation and traction, activated manually, with respective clamping means, such as for example one or more clamping pegs 19, thus causing the stable mechanical connection of the free multiple connector 14 to the static and fixed multiple counter-connector 15 with which it is coupled. The clamping pegs 19 can for example be advantageously protruding from a lateral surface, for example in particular from the bushing 26a, of the connector support body 26 of the free multiple connector 14. Furthermore, the clamping bushing 24 can be configured for example so that, with a movement of inverse rotation, desired and not accidental, it is possible to release the releasable manual mechanical clamping device 16 and disconnect the free multiple connector 14 from the static and fixed multiple counter-connector 15. The clamping bushing 24 and the clamping pegs 19 can obtain overall a conversion unit, for example with inclined planes as will be described in more detail hereafter, to convert a rotation motion, clock-wise or anti-clockwise, into a traction motion, in order to obtain respectively the attachment/detachment of the free multiple connector 14 to/from the static and fixed multiple counter-connector 15.

In possible forms of embodiment, which can be combined with all the forms of embodiment described here, a drive lever 20 may be provided, protruding from the clamping bushing 24, which can be driven manually by the operator to make the clamping bushing 24 rotate and to act in traction on the clamping peg 19, thus obtaining the desired mechanical clamping, with an easy and comfortable movement and without needing complicated and bulky pneumatic actuation systems. The angular position of the drive lever 20 on the clamping bushing 24 can be chosen so that it is ergonomically easy for the operator to intervene thereon, and to rotate the clamping mechanism, whether acting always from one side (machine with one door), or acting from two sides (pass-through machine).

In some forms of embodiment, the clamping bushing 24 can advantageously be included in the static and fixed multiple counter-connector 15, and can be configured to house the counter-connector support body 25 and also to receive, at least partly inserted inside it, and to clamp the connector support body 26 of the free multiple connector 14. For example, the clamping bushing 24 can include a lateral mantle 24a, typically cylindrical, which internally delimits a housing aperture 24b.

In possible implementations, the clamping bushing 24 can include one or more inclined clamping slots 18, configured to cooperate with one or more respective clamping pegs 19.

For example, in possible implementations, the one or more inclined clamping slots 18 can be made by through notches made in the lateral mantle 24a of the clamping bushing 24.

In some forms of embodiment, which can be combined with all the forms of embodiment described here, the one or more inclined clamping slots 18 are configured as an inclined plane to convert a rotation motion into a linear traction motion, cooperating with the one or more clamping pegs 19, of the free multiple connector 14 toward the static and fixed multiple counter-connector 15.

For example, the one or more inclined clamping slots 18 can be delimited by an open clamping profile 18a, configured to transform a rotation movement of the clamping bushing 24 around its central axis into a linear movement of axial traction exerted on the respective clamping peg 19 in order to clamp the connector support body 26 to it.

In particular, in possible implementations given by way of example, the inclined clamping slot 18 defined by the clamping profile 18a can have an entrance 18b to receive the respective clamping peg 19, an inclined plane 18c along which the clamping peg 19 can slide, for example defined by a linear segment inclined with respect to the central axis of the clamping bushing 24, or a curvilinear segment, an arc of a circle, or a helical segment around the central axis, and finally a stop and support segment 18d, for example transverse to the central axis, in which the clamping peg 19 is stably clamped, advantageously abutting against an end-of-travel bottom 18e.

In some forms of embodiment, which can be combined with all the forms of embodiment described here, a single inclined clamping slot 18 and a respective clamping peg 19 may be sufficient. Otherwise, in other forms of embodiment (see FIG. 4 for example) two inclined clamping slots 18 can be provided, symmetrical in the clamping bushing 24, with respective clamping pegs 19.

In possible implementations, the clamping bushing 24 can be attached for example to the assembly plate 32 used to assemble the static and fixed multiple counter-connector 15 in the washing chamber 11. For example, a fluid-sealing packing can be provided, such as an O-ring or similar annular packing, between clamping bushing 24 and assembly plate 32. To allow the passage of the connection sockets 31 to which the pipes of the washing circuit of the washer machine 10 are connected, the assembly plate 32 can have a suitable connection aperture 33 (see FIGS. 3 and 4 for example).

In some forms of embodiment, which can be combined with all the forms of embodiment described here, the releasable manual mechanical clamping device 16 can include a guide and centering unit 40, configured to function as a reference and to promote the correct and centered coupling of the free multiple connector 14 and the static and fixed multiple counter-connector 15.

In possible implementations, the guide and centering unit 40 can include for example a centering peg 28, protruding from the free multiple connector 14, for example from the connector support body 26 (see FIGS. 3 and 4 for example).

Furthermore, the guide and centering unit 40 can include for example a centering hole 29, in a coordinated position on the static and fixed multiple counter-connector 15, to receive the centering peg 28 and thus achieve a quick and precise reference for connecting the free multiple connector 14 and the static and fixed multiple counter-connector 15 in a correct and centered manner, so that there is a correct multiple connection between all the individual connectors 21 and the respective individual counter-connectors 22. It is clear that, as an alternative, it may be possible to provide the centering peg 28 on the static and fixed multiple counter-connector 15 and the centering hole 29 on the free multiple connector 14.

In some forms of embodiment, the washer machine 10 can include a single washing device 12 and a respective single sliding loader trolley 13.

In other forms of embodiment, described for example using FIG. 1, the washer machine 10 can include a plurality of washing devices 12. Consequently, a plurality of free multiple connectors 14 may be provided, and an equal number of static and fixed multiple counter-connectors 15 mounted on the washer machine 10, in particular disposed for example vertical, typically at a defined pitch, in the washing chamber 11, in particular on one of the lateral walls 11a thereof. In a coordinated manner, a plurality of sliding loader trolleys 13 may be provided, for example positionable vertical in the washing chamber 11, which allow to position and load one or more endoscopic instruments on each of them. For example, two, three, four or even more than four sliding loader trolleys 13 may be provided.

In some forms of embodiment, which can be combined with all the forms of embodiment described here, the one or more sliding loader trolleys 13 can each have a support plane with a grid-like structure 45, which for example promotes the passage of the water, on which the endoscopic instrument to be treated is positioned, or the transport tray, also for example with a grid-like structure, which can be used to transport and contain during transport the endoscopic instrument already connected to the respective free multiple connector 14 and corresponding flexible washing pipes 17, in turn already connected to the endoscopic instrument.

In some forms of embodiment, which can be combined with all the forms of embodiment described here, the one or more sliding loader trolleys 13 can be selectively mobile by means of sliding elements 46, in this case wheels, positioned on the internal surface of the washing chamber 11 and selectively coupled with guides 47 provided at the sides of the sliding trolley 13, or vice versa, providing the sliding elements 46 on the sliding loader trolley 13 and the guides 47 in the washing chamber 11.

In some forms of embodiment, the one or more sliding loader trolleys 13 can be selectively provided removable from the washing chamber 11.

Typically, the washer machine 10 can include at least one entrance door 34, by means of which to access the washing chamber 11 and to close it during the treatment cycle.

For example, the at least one entrance door 34 can be the type that slides vertically, for example the guillotine type, or with rotating opening, upward or downward, retractable or not, pivoting horizontally or tilting.

The washer machine 10 can be the type with a single door, which functions as both entrance and exit, or a double door ("pass-through"), in which an entrance door and an exit door are provided on two opposite sides of the washer machine 10 so as to enter the washing chamber 11 on one side and to exit from it on the opposite side.

In some forms of embodiment, which can be combined with all the forms of embodiment described here, the washer machine 10 can generally include an external frame 35, with an essentially vertical development, more or less accentuated depending on the number of sliding loader trolleys 13 and washing devices 12 provided.

The washing chamber 11 is provided inside the external frame 35, and also electric and hydraulic components and systems, needed for the functioning of the washer machine 10, can be housed therein.

Thanks to the fact that no pneumatic actuation head to connect the multiple connector is provided inside the bulk of the external frame 35, as instead happens in the state of the art, the washer machine 10 according to the present description is all in all more compact, less complex and less costly.

It is clear that modifications and/or additions of parts may be made to the washer machine 10 as described heretofore, without departing from the field and scope of the present invention.

It is also clear that, although the present invention has been described with reference to some specific examples, a person of skill in the art shall certainly be able to achieve many other equivalent forms of washer machine, having the characteristics as set forth in the claims and hence all coming within the field of protection defined thereby.

The invention claimed is:

1. Washer machine for medical instruments, each of the medical instruments including an aperture, the washer machine comprising:
   a washing chamber,
   a sliding loader trolley arranged to load the medical instruments into the washing chamber,
   a washing device to wash the medical instruments, the washing device comprising a multiple connection unit and a plurality of flexible washing pipes each connectable to a corresponding aperture of the medical instruments to be washed,
   said multiple connection unit comprising:
   a free multiple connector, autonomous and unconstrained from the sliding loader trolley and connectable to said flexible washing pipes, and
   a static and fixed multiple counter-connector, mounted fixed in the washing chamber,
   wherein said free multiple connector comprises a plurality of individual connectors, each of the plurality of individual connectors also unconstrained from the sliding loader trolley and further being connectable on one side to said flexible washing pipes and on another side connectable to mating individual counter-connectors provided in the static and fixed multiple counter-connector,
   a releasable manual mechanical clamping device being provided for the selective connection of the free multiple connector to the static and fixed multiple counter-connector, the releasable manual mechanical clamping device comprising a conversion unit including a bushing having a drive lever and one or more inclined slots; and
   wherein the free multiple connector comprises a connector support body and a flexible pipe collector body, both unconstrained from the sliding loader trolley, the connector support body including at least one clamping peg and being configured to support said plurality of individual connectors, and the flexible pipe collector body having a central through cavity sized for the passage of the plurality of flexible washing pipes, wherein the at least one clamping peg is inserted into the one or more inclined slot of the bushing such that manual engagement of the drive lever causes the bushing to rotate and urge the at least one clamping peg into a traction motion to detach the free multiple connector from the static and fixed multiple counter-connector and to attach the free multiple connector and the static and fixed multiple counter-connector.

2. The washer machine as in claim 1, wherein the bushing further comprises a transverse wall supporting individual connector holes, each of the individual connector holes arranged to engage a corresponding one of the individual connectors, and wherein the flexible pipe collector body includes a protruding tang.

3. The washer machine as in claim 1, wherein the static and fixed multiple counter-connector comprises a counter-connector support body, configured to support the individual counter-connectors.

4. The washer machine as in claim 1, wherein said releasable manual mechanical clamping device is a rotary type clamping device.

5. The washer machine as in claim 1, wherein said releasable manual mechanical clamping device comprises a clamping bushing configured to cooperate in rotation and traction with respective clamping means, determining the mechanical connection of the free multiple connector to the static and fixed multiple counter-connector.

6. The washer machine as in claim 5, wherein the clamping bushing is comprised in the static and fixed multiple counter-connector and the clamping means are comprised in the free multiple connector.

7. The washer machine as in claim 5, wherein the one or more inclined clamping slots convert a rotation motion of the free multiple connector, insertable and rotatable in said one or more inclined clamping slots, into a linear traction motion, cooperating with said clamping means, of the free multiple connector toward the static and fixed multiple counter-connector.

8. The washer machine as in claim 1, wherein said releasable manual mechanical clamping device comprises a guide and centering unit configured for the correct and centered coupling of the free multiple connector and the static and fixed multiple counter-connector.

9. Washer machine for medical instruments, each of the medical instruments including an aperture, the washer machine comprising:
a washing chamber,
a sliding loader trolley arranged to load the medical instruments into the washing chamber,
a washing device to wash the medical instruments, the washing device comprising a multiple connection unit and a plurality of flexible washing pipes, each of the flexible washing pipes being connectable to a corresponding aperture of the medical instruments to be washed,
the multiple connection unit comprising:
a free multiple connector that is autonomous and unconstrained from the sliding loader trolley and connectable to said flexible washing pipes, the free multiple connector including a connector support body and a flexible pipe collector body, both unconstrained from the sliding loader trolley, the connector support body configured to support a plurality of individual connectors, and the flexible pipe collector body having a central through cavity sized for the passage of the plurality of flexible washing pipes; and
a static and fixed multiple counter-connector, mounted fixed in the washing chamber,
the plurality of individual connectors each being connectable on one side to said flexible washing pipes and on another side connectable to mating individual counter-connectors provided in the static and fixed multiple counter-connector,
wherein the free multiple connector and the static and fixed multiple counter-connector are aligned by a centering peg, the centering peg extending between the connector support body of the free multiple connector and a support bushing carried by the static and fixed multiple counter-connector; and
a releasable rotary manual mechanical clamp carried by the static and fixed multiple counter-connector and arranged to connect and disconnect the free multiple connector to the static and fixed multiple counter-connector, the rotary mechanical clamp including a rotatable bushing having a drive lever, and an inclined clamping slot arranged to engage a clamping peg, wherein manual engagement of the drive lever causes the bushing to rotate and urge the at least one clamping peg into a traction motion to detach the free multiple connector from the static and fixed multiple counter-connector and to attach the free multiple connector and the static and fixed multiple counter-connector.

* * * * *